(12) United States Patent
Prisco

(10) Patent No.: US 8,358,883 B2
(45) Date of Patent: *Jan. 22, 2013

(54) FIBER OPTIC SHAPE SENSOR

(75) Inventor: Giuseppe Maria Prisco, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/366,534

(22) Filed: Feb. 6, 2012

(65) Prior Publication Data

US 2012/0132009 A1    May 31, 2012

Related U.S. Application Data

(63) Continuation of application No. 12/764,307, filed on Apr. 21, 2010, now Pat. No. 8,116,601, which is a continuation of application No. 12/164,829, filed on Jun. 30, 2008, now Pat. No. 7,720,322.

(51) Int. Cl.
*G02B 6/00* (2006.01)
*B25J 17/00* (2006.01)
(52) U.S. Cl. ........................ 385/12; 74/490.01
(58) Field of Classification Search .............. 385/12, 385/13
See application file for complete search history.

(56) References Cited

U.S. PATENT DOCUMENTS

| | | | |
|---|---|---|---|
| 4,443,698 A | 4/1984 | Schiffner | |
| 5,563,967 A | 10/1996 | Haake | |
| 5,641,956 A | 6/1997 | Vengsarkar et al. | |
| 5,798,521 A | 8/1998 | Froggatt | |
| 6,127,672 A * | 10/2000 | Danisch | 250/227.14 |
| 6,256,090 B1 | 7/2001 | Chen et al. | |
| 6,301,420 B1 | 10/2001 | Greenaway et al. | |
| 6,389,187 B1 | 5/2002 | Greenaway et al. | |
| 6,471,710 B1 * | 10/2002 | Bucholtz | 606/130 |
| 6,571,639 B1 | 6/2003 | May et al. | |
| 6,671,055 B1 | 12/2003 | Wavering et al. | |
| 6,856,400 B1 | 2/2005 | Froggatt | |
| 6,888,623 B2 | 5/2005 | Clements | |
| 6,898,337 B2 | 5/2005 | Averett et al. | |
| 6,900,897 B2 | 5/2005 | Froggatt | |
| 7,042,573 B2 | 5/2006 | Froggatt | |
| 7,330,245 B2 | 2/2008 | Froggatt | |

(Continued)

FOREIGN PATENT DOCUMENTS

WO    WO 2008094949    8/2008

OTHER PUBLICATIONS

Froggatt, Mark and Jason Moore, "Distributed measurement of static strain in an optical fiber with multiple Bragg gratings at nominally equal wavelengths," Journal of Applied Optics, Apr. 1, 1998, vol. 37, Issue 10, pp. 1741-1746.

(Continued)

*Primary Examiner* — Charlie Peng

(57) ABSTRACT

A shape sensing system to determine the position and orientation of one link with respect to another link in a kinematic chain. An optical fiber is coupled to two or more links in a kinematic chain. A shape sensing segment is defined to start at a proximal link and to end at a distal link, crossing one or more joints. A reference frame is defined at the start of the shape sensing segment. As the joints move, an interrogator senses strain in the shape sensing segment. The sensed strain is used to output a Cartesian position and orientation of the end of the shape sensing segment with respect to the reference frame defined at the start of the shape sensing segment. The pose of the kinematic chain is determined from the Cartesian positions and orientations of one or more shape sensing segments defined for the kinematic chain and from an a priori model and constraints of the kinematic chain.

2 Claims, 8 Drawing Sheets

U.S. PATENT DOCUMENTS

| | | |
|---|---|---|
| 7,440,087 B2 | 10/2008 | Froggatt et al. |
| 2001/0021843 A1* | 9/2001 | Bosselmann et al. ............ 606/2 |
| 2002/0097960 A1 | 7/2002 | Greenaway et al. |
| 2006/0013523 A1 | 1/2006 | Childlers et al. |
| 2007/0065077 A1 | 3/2007 | Childers et al. |
| 2007/0151390 A1 | 7/2007 | Blumenkranz et al. |
| 2007/0151391 A1 | 7/2007 | Larkin et al. |
| 2007/0156019 A1 | 7/2007 | Larkin et al. |
| 2007/0265503 A1 | 11/2007 | Schlesinger et al. |
| 2007/0287992 A1 | 12/2007 | Diolaiti et al. |
| 2008/0065105 A1 | 3/2008 | Larkin et al. |
| 2008/0065111 A1 | 3/2008 | Blumenkranz et al. |
| 2008/0212082 A1 | 9/2008 | Froggatt et al. |
| 2008/0218770 A1 | 9/2008 | Moll et al. |
| 2008/0234631 A1 | 9/2008 | Reis |
| 2008/0243064 A1 | 10/2008 | Stahler et al. |
| 2008/0249536 A1 | 10/2008 | Stahler et al. |
| 2008/0255505 A1 | 10/2008 | Carlson et al. |
| 2008/0262513 A1 | 10/2008 | Stahler et al. |
| 2008/0275367 A1 | 11/2008 | Barbagli et al. |
| 2008/0285909 A1 | 11/2008 | Younge et al. |
| 2008/0294144 A1* | 11/2008 | Leo et al. ...................... 604/508 |
| 2009/0024141 A1 | 1/2009 | Stahler et al. |
| 2009/0076476 A1 | 3/2009 | Barbagli et al. |
| 2009/0123111 A1 | 5/2009 | Udd |
| 2009/0137952 A1 | 5/2009 | Ramamurthy et al. |
| 2009/0138025 A1 | 5/2009 | Stahler et al. |

OTHER PUBLICATIONS

Kersey, Alan D. et al., "Fiber Grating Sensors," Journal of Lightwave Technology, vol. 15, No. 8, pp. 1442-1463, Aug. 1997.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

FIBER OPTIC SHAPE SENSOR

CROSS REFERENCE TO RELATED APPLICATION

This application is a continuation of U.S. patent application Ser. No. 12/764,307 (filed Apr. 21,2010, now U.S. Pat. No. 8,116,601) which is a continuation of U.S. patent application Ser. No. 12/164,829 (filed Jun. 30, 2008; now U.S. Pat. No. 7,720,322), which are incorporated herein by reference

BACKGROUND

1. Field of Invention

Inventive aspects are associated with shape sensing, more particularly to sensing position and orientation at various points of a kinematic chain, and still more particularly to sensing the shape of a flexible body and sensing the position and orientation of an end effector component of a surgical instrument or of an entry guide for one or more surgical instruments in a telerobotic surgical system.

2. Background Art

FIG. 1 is a diagrammatic view of an optical fiber core portion 100. The surrounding cladding and fiber are omitted for clarity. Two fiber Bragg gratings (FBG's) 102a,102b are shown formed in fiber core portion 100, which are illustrative of many such FBG's typically formed along the full length of a core. The many vertical lines shown in each FBG 102 represent the changes in refractive index that characterize an FBG. As shown in FIG. 1, the FBG's 102a,102b are separated by a tether segment 104, which is completely transmissive.

As is known, each of the FBG's 102 may be interrogated for strain information. In a fiber that contains two or more cores, with FBG's in each core positioned at the same location along the fiber, the fiber's bend direction and amount of axial twist may be determined from the strains in each core's FBG's. From the strain information from each core at each FBG location, and from the known tether segment length (e.g., 5 mm, 1 cm), the position of the location with the next set of FBG's can be estimated. In this way, the fiber shape associated with the interrogated FBG's may be determined. U.S. Pat. App. Publ. No. US 2006/0013523 A1 (filed 13 Jul. 2005), which is incorporated herein by reference, discloses a fiber optic position shape sensing device and method. In one instance, strain information is used to determine the bend angle between two links, as described in U.S. Pat. App. Publ. No. US 2007/0156019 A1 (filed 20 Jul. 2006), which is incorporated herein by reference. Such bend information may be used in forward kinematic calculations to determine the position of the distal end of a kinematic chain (a set of links coupled by one or more movable mechanical constraints). One non-limiting example of such a kinematic chain is a minimally invasive surgical instrument with one or more revolute joints.

In one instance, a curvilinear coordinate system is defined with an origin at the connection where the fiber is joined to the interrogator unit (i.e., at the proximal end of the fiber). In addition, a Cartesian frame is also defined as a base reference frame having an origin coincident with the curvilinear coordinate system's origin. Using known techniques, each of the FBG's 102 are interrogated for strain information.

Known techniques to interrogate the FBG's by processing the light reflected back when an optical light source is coupled with the fiber are described in, for instance, Andreas Othonos & Kyriacos Kalli, *Fundamentals and Applications in Telecommunications and Sensing* Ch. 7, 301-388 (Arthech House 1999), which is incorporated herein by reference. Such interrogation techniques include on the use of edge filters, tunable filters, interferometers, tunable lasers, and CCD spectrometers. Each technique provides different spatial resolution in the measurement of strain along a fiber core, different speeds of interrogation, i.e., update of the measurement, and different levels of immunity to disturbances to the strain measurements such as those produced by variation of temperature, light polarization, source light variations, and losses of light along the fiber. Among the interferometric techniques that are based on detection of the phase of the reflected light are Optical Time Domain Reflectometry and Optical Frequency Domain Reflectometry (OFDR), as described in U.S. Pat. No. 5,798,521 (filed 27 Feb. 1997) and in U.S. Pat. App. Publ. No. US 2007/0065077 A1 (filed 26 Sep. 2006), which are incorporated herein by reference.

To determine the fiber's approximate shape, the strain information measured at each FBG location is used to determine the approximate local bend for the length of fiber without FBG's (e.g., over a 1 cm tether segment). For example, the strain information from three cores in a fiber is used to compute the plane and the bend radius of the fiber. Segments are defined at various locations along the fiber, and each segment ends at a co-located ring of FBG's in the three cores. Given the Cartesian x,y,z position of the FBG ring being processed (i.e., the segment end position), the position of the next FBG ring can be computed with simple geometry. The position of the first segment's end location with respect to the base frame is then determined from the first segment's bend information. Next, strain information for the second segment is processed to determine the second segment's bend. The second segment's bend information is combined with the position of the first segment's end location to determine the second segment's end location position with respect to the base frame. Thus the position of each segment end location is determined with respect to the base frame, and the position information is used to determine the approximate shape of the fiber.

There are, however, disadvantages to current optical fiber shape sensing methods. To begin with, such methods are based on the average strain measured in each FBG, and so the FBG size limits the measurement resolution. In addition, the shape (or state) of the fiber is reconstructed as a vector of equally spaced three-dimensional (3D) points in world coordinates. The result is a large data set that gets larger as measurement resolution is increased. Also, the resolution of the 3D points is limited by the spacing between FBG's. Further, in these methods there is an assumption that the length of fiber between measured FBG's has a constant bend radius, and this assumption can reduce the accuracy of the sensed shape as compared with the fiber's actual shape. Another disadvantage is that the computation of the fiber tangent vector at a particular fiber location (i.e., the direction the fiber is pointing at that location) requires differentiation of the 3D points. This differentiation delivers even lower measurement resolution. Yet another disadvantage is that the 3D point data set is not in a form that is required for the type of processing needed when the fiber is embedded into a kinematic chain, and therefore the kinematic chain's pose has to be inferred from the sensed fiber position. This limitation is especially true if the fiber is embedded in a kinematic chain but is allowed to slide with reference to one or more links. In such configurations, the fiber may not follow a path that exactly corresponds to a bend in one or more of the kinematic chain's joints, and friction between the fiber's surface and a surrounding conduit through one or more links may influence the fiber's shape.

What is needed, therefore, is a more effective and accurate way to determine the shape of an optical fiber and a more effective way of producing the shape information for use in determining the position and orientation of all the links of a kinematic chain, i.e., the pose of a kinematic chain, that is associated with the fiber. These needs are especially true for various real time implementations, such as for telerobotically controlled minimally invasive surgical instruments.

SUMMARY

A shape sensing system to determine the position and orientation of one link with respect to another link in a kinematic chain is described. An optical fiber is coupled to two or more links in a kinematic chain. A shape sensing segment is defined to start at a proximal link and to end at a distal link, crossing one or more joints. A reference frame is defined at the start of the shape sensing segment. The reference frame may be defined in various ways, and one way is to define one axis normal to the fiber and another axis tangent to the fiber.

As the joints move, an interrogator senses strain in the shape sensing segment. The sensed strain is used to output a Cartesian position and orientation of the end of the shape sensing segment with respect to the reference frame defined at the start of the shape sensing segment. The Cartesian position and orientation may be used to define a reference frame for a subsequent shape sensing segment for one or more additional links and joints in the kinematic chain. The Cartesian position and orientation is determined and output in a format that facilitates calculation. The pose of the kinematic chain is determined from the Cartesian positions and orientations of one or more shape sensing segments defined for the kinematic chain, from an a priori model of the kinematic chain, and from the geometrical constraints between the shape sensing fiber and the kinematic chain.

DETAILED DESCRIPTION

Figure 1:
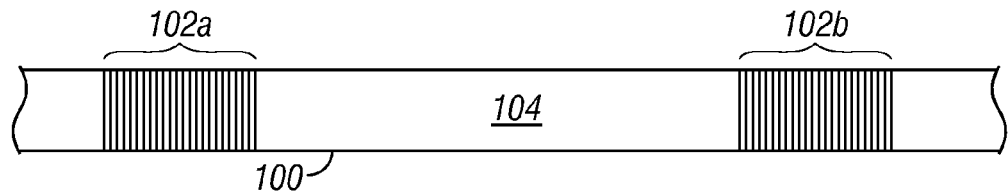
FIG. 1 is a diagrammatic view of an optical fiber core portion.

This description and the accompanying drawings that illustrate aspects and embodiments of the present invention should not be taken as limiting—the claims define the protected invention. Various mechanical, compositional, structural, electrical, and operational changes may be made without departing from the spirit and scope of this description and the claims. In some instances, well-known circuits, structures, and techniques have not been shown or described in detail in order not to obscure the invention. Like numbers in two or more figures represent the same or similar elements.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings.

The term "flexible" in association with a mechanical structure or component should be broadly construed. In essence, it means the structure or component can be bent without harm. For example, a flexible mechanical structure may include a series of closely spaced components that are similar to "vertebrae" in a snake-like arrangement. In such an arrangement, each component is a short link in a kinematic chain, and movable mechanical constraints (e.g., pin hinge, cup and ball, and the like) between each short link may allow one (e.g., pitch) or two (e.g., pitch and yaw) degrees of freedom (DOF) of relative movement between the links. As another non-limiting example, a flexible mechanical structure may be continuous, such as a closed, bendable tube (e.g., Nitinol, polymer, and the like) or other bendable piece (e.g., kerf-cut tube, helical coil, and the like). Accordingly, a short, flexible structure may serve as, and be modeled as, a single mechanical constraint (joint) providing one or more DOF's between two links in a kinematic chain, even though the flexible structure itself may be a kinematic chain made of several coupled links.

I. Fiber Optic Shape Sensor

Figure 2:
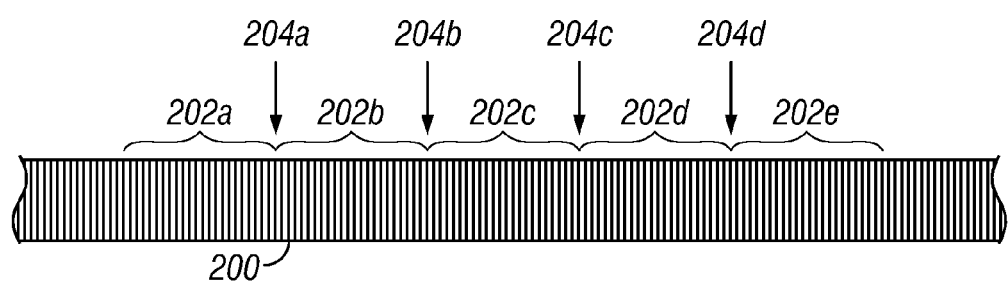
FIG. 2 is a diagrammatic view of another optical fiber core portion.

FIG. 2 is a diagrammatic view of another optical fiber core portion 200. The surrounding cladding and fiber are omitted for clarity. Core portion 200 shows illustrative FBG's 202a-202e formed adjacent one another in the optical fiber core. There is no tether segment between the FBG's. In some instances a boundary region, illustrated by regions 204a-204d, separates adjacent FBG's such that the spacing between the refractive index changes in each FBG 202a-202e may not be exactly the same as the spacing between FBG's. Again, the many vertical lines shown in each FBG 202 represent the changes in refractive index that characterize an FBG.

A distinctive feature of using OFDR, and interferometric techniques in general, for strain interrogation with a fiber as illustrated by FIG. 2 is that it allows sensing the strain in the fiber over the FBG's with a very high resolution—on the order of microns for fibers of 10 m length—as determined by the interrogating laser source coherence length.

FIGS. 3A-3E are diagrammatic views of various configurations of optical fiber cores. The surrounding cladding and fiber are omitted for clarity. Each of the many vertical lines shown in the illustrative cores represent individual, adjacent FBG's (e.g., FBG's 202a-202e as shown in FIG. 2). In one embodiment, approximately 60 FBG's are formed for every 20 mm length of a core/fiber. As described below, each core is one of three or more cores in a single fiber.

Figure 3A:
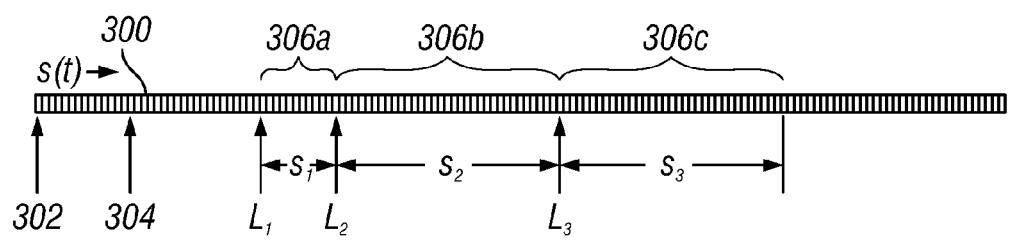
FIGS. 3A-3E are diagrammatic views of optical fiber cores.

As shown in FIG. 3A, a curvilinear coordinate system s(t) is defined for the fiber, and hence for core 300 and the other cores (not shown). In some cases the location $L_0$ of the origin of s(t) is defined at the proximal end 302 of the fiber, where the fiber connects to a strain information interrogator unit. In other cases, the origin location $L_0$ of s(t) may be defined at a location 304 along the fiber. For example, $L_o$ may be defined at a location within a base mechanical link of a kinematic chain at which the fiber is fixed during manufacturing.

Then, once the origin location is defined, one or more shape sensing segments (bend segments) are defined between locations along the core. Each defined shape sensing segment of a core contains part of one FBG, or one full FBG, or many adjacent FBG's. As shown in FIG. 3A, for example, three shape sensing segments 306a-306c are defined. Each shape sensing segment is defined in s(t) as beginning at a segment start location on the fiber and continuing along for a particular segment length until a segment end location on the fiber. As shown in FIG. 3A, for example, segment 306a begins at a first location $L_1$ and continues for length $s_1$. Similarly, segment 306b begins at segment start location $L_2$ and continues for length $s_2$, and segment 306c begins at segment start location $L_3$ and continues for length $s_3$. Segments of equal length (e.g., segments 306b,306c as shown) or of different lengths (e.g., segments 306a,302b as shown) may be defined. In addition, the shape sensing segments need not be adjacent one another—they can be defined to overlap. And, the most distal shape sensing segment may or may not be defined to end at the distal end of the fiber.

Figure 3B:
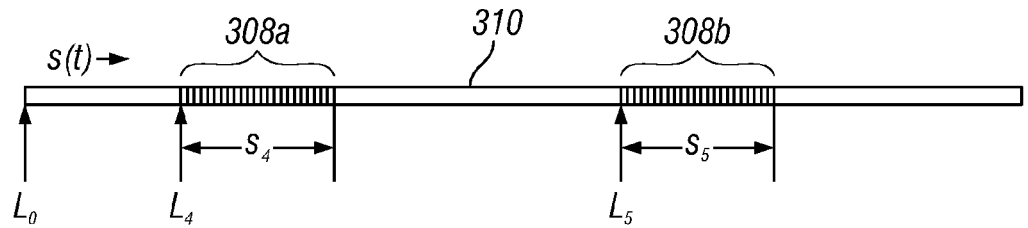

FIG. 3B illustrates a fiber core similar to the core illustrated in FIG. 3A, but which has segments 308a,308b of adjacent FBG's separated by a fiber length 310 without FBG's. This configuration differs from the one illustrated in FIG. 1, in which each FBG is separated by a tether segment. A configuration as illustrated by FIG. 3B may be used, for example, in a kinematic chain with long, straight links coupled by revolute joints. Each segment 308a,308b is positioned to correspond to a joint and is used to sense fiber strain associated with the corresponding joint's movement. The length 310 is positioned to correspond to a long, rigid portion of a link (see e.g., the link illustrated in FIGS. 9A-9C below). Since the long, rigid link never bends, sensing the fiber's shape within the link is not required. The segments 308a,308b are used to sense the relative position and orientation between adjacent links. The most distal FBG segment may be placed at the most distal end of the fiber, or a fiber length without FBG's may exist between the most distal FBG segment and the fiber's distal end.

Figure 3C:
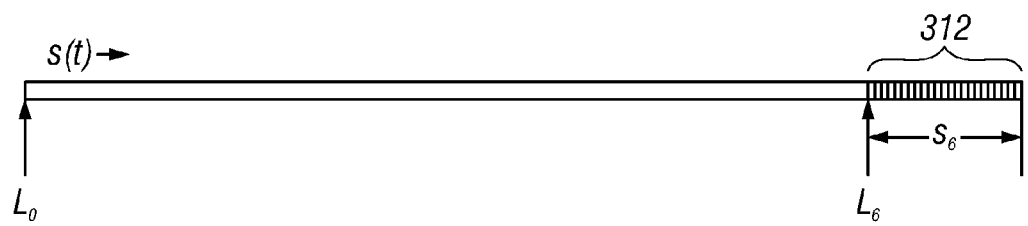

FIG. 3C also illustrates a fiber core similar to the core illustrated in FIG. 3A, but which has only a single segment 312 of adjacent FBG's at the fiber's distal end. A configuration as illustrated by FIG. 3C may be used, as a non-limiting example, to sense only movement of a distal portion of a kinematic chain (e.g., only the position and/or orientation of an end effector at the distal end of a minimally invasive surgical instrument, and/or the position of a jaw in a jawed end effector (grasper, scissors, and the like)).

Figure 3D:
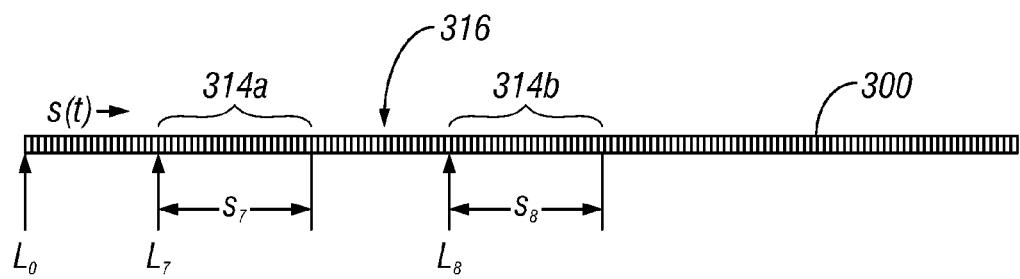
Figure 3E:
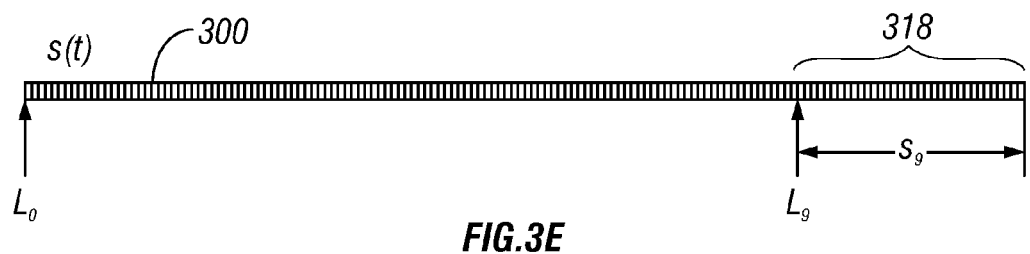

FIGS. 3D and 3E are similar to FIGS. 3B and 3C, but the cores in FIGS. 3D and 3E have FBG's defined along their entire length, although segments are defined in non-adjacent FBG portions of the core. As shown in FIG. 3D, for example, segments 314a and 314b are defined with a length 316 of FGB-configured core between them. As shown in FIG. 3E, segment 318 is defined at the distal end of the core, with no additional segments defined in the FBG-configured core.

Figure 4A:
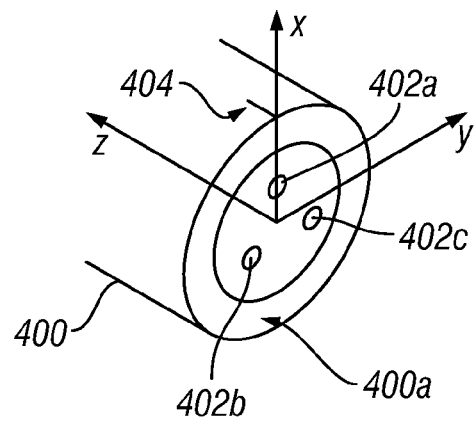
FIGS. 4A and 4B are diagrammatic views of the proximal ends of optical fibers with an illustrative reference frame.

FIG. 4A is a diagrammatic view of the proximal end of an optical fiber 400 with an illustrative reference frame defined. As shown in FIG. 4A, fiber 400 has three FBG-configured cores 402a-402c within a cladding layer 404. Each core 402a-402c is positioned at an apex of an equilateral triangle centered in the fiber.

As shown in FIG. 4A, a Cartesian reference frame is defined for the fiber 400. One axis of the Cartesian reference frame intersects one of the cores (the x-axis is shown intersecting core 402a as an illustration) and another axis is tangent to the fiber 400's centerline (the z-axis is shown as an illustration). Defining the x-axis to extend through a core provides a rotational reference around core 400's centerline. The definition of the x-axis is arbitrary and can be based on the geometry of the kinematic chain embedding the fiber. For instance, the x-axis could be aligned to one joint axis of the kinematic chain in which the fiber is embedded or associated.

The Cartesian reference frame (x, y, z) shown in FIG. 4A functions as a base frame when defined with an origin coincident with the origin of the curvilinear coordinate system s(t). When a Cartesian reference frame is defined with an origin at a segment start location, it functions as a shape sensing segment reference frame. A Cartesian reference frame may be similarly defined at a segment end location.

Figure 4B:
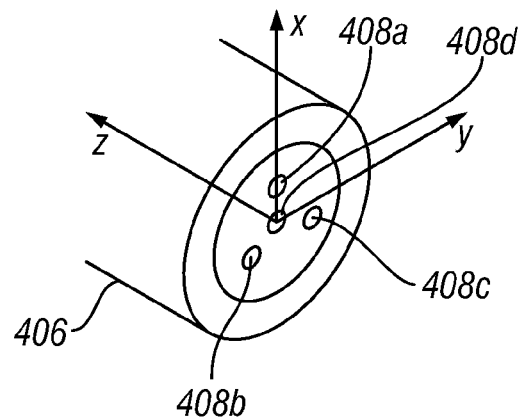

Although three cores are shown in FIG. 4A, other numbers of cores may be used (e.g., two opposite cores for planar bend measurement, four cores, etc.). FIG. 4B is a diagrammatic view of the proximal end of another optical fiber 406. As shown in FIG. 4B, fiber 406 has four FBG-configured cores 408a-408d within a cladding layer. Each core 408a-408c is positioned at an apex of an equilateral triangle centered in the fiber, and core 408d is positioned at the center of the equilateral triangle, which is coincident with the center of the fiber. Once again, an x-axis is defined intersecting a core (408a) at an apex. The z-axis originates tangent to the core 408d at the center of the triangle. The center core 408d may be used to enable sensing the angle of torsion around the fiber's center longitudinal axis (strain between cores at the apexes, which varies with torsion of the fiber, is compared to strain in the core at the center, which does not vary with torsion of the fiber).

In comparison, fibers without such a center core (e.g., the three-core fiber illustrated in FIG. 4A) cannot be used to sense the fiber's angle of torsion. For this reason, fibers without a center core are used in mechanical configurations that minimize torsional loads. In such configurations, since the fiber has an inherent degree of torsional stiffness, the x-axes of each reference frame defined along the fiber's length maintain an essentially constant rotational relationship to each other around the fiber's centerline.

Figure 5:
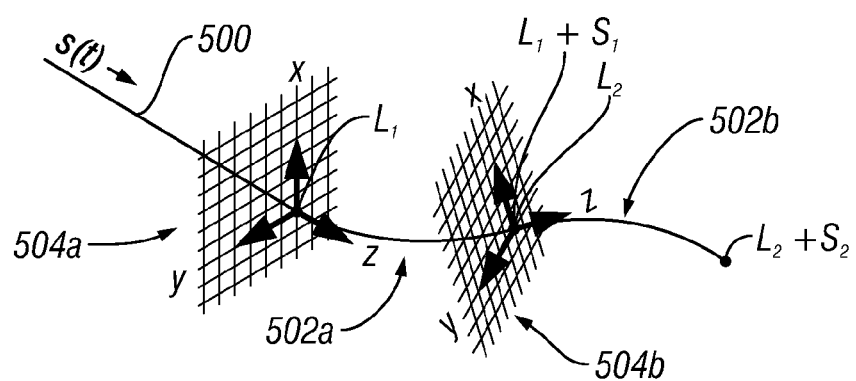
FIG. 5 is a diagrammatic view that illustrates reference frames at segment start locations in an optical fiber used for shape sensing.

FIG. 5 is a diagrammatic view that illustrates reference frames at segment starts in an optical fiber used for shape sensing. FIG. 5 depicts an optical fiber 500 that is, in one embodiment, configured with three cores as illustrated in FIG. 4A (four cores as illustrated above, or other core configurations, may be used). In this illustrative example, each core is configured as shown in FIG. 3A, although various FBG configurations may be used, as described above. Two shape sensing segments are defined in fiber 500. The first segment 502a is defined from curvilinear reference location $L_1$ (segment start) to curvilinear reference location $L_1+s_1$ (segment end). The second segment 502b is defined from curvilinear reference location $L_2$ (segment start) to curvilinear reference location $L_2+s_2$ (segment end). In accordance with an aspect of the invention, a first Cartesian reference frame 504a is defined at segment start $L_1$. Reference frame 504a's z-axis is tangent to the centerline of fiber 500 at segment start $L_1$, and reference frame 504a's x-axis runs through one of the cores as illustratively shown and described in FIG. 4A. Similarly, a second Cartesian reference frame 504b is defined at segment start $L_2$, with reference frame 504b's z-axis tangent to the centerline of fiber 500 at segment start $L_2$, and reference frame 504b's x-axis running through the same core as reference frame 504a's x-axis.

The base reference frame illustrated in FIG. 4A and the two segment start reference frames illustrated in FIG. 5 are interrelated because all three have one normal axis (e.g., the x-axis) defined through the same core (e.g., core 402a).

Figure 6A:
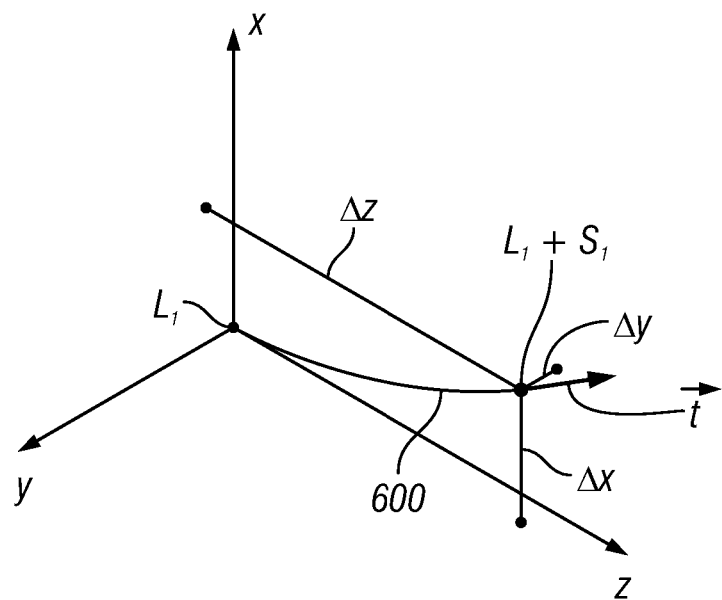
FIGS. 6A and 6B are diagrammatic views that illustrate determining segment end position and orientation.
Figure 6B:
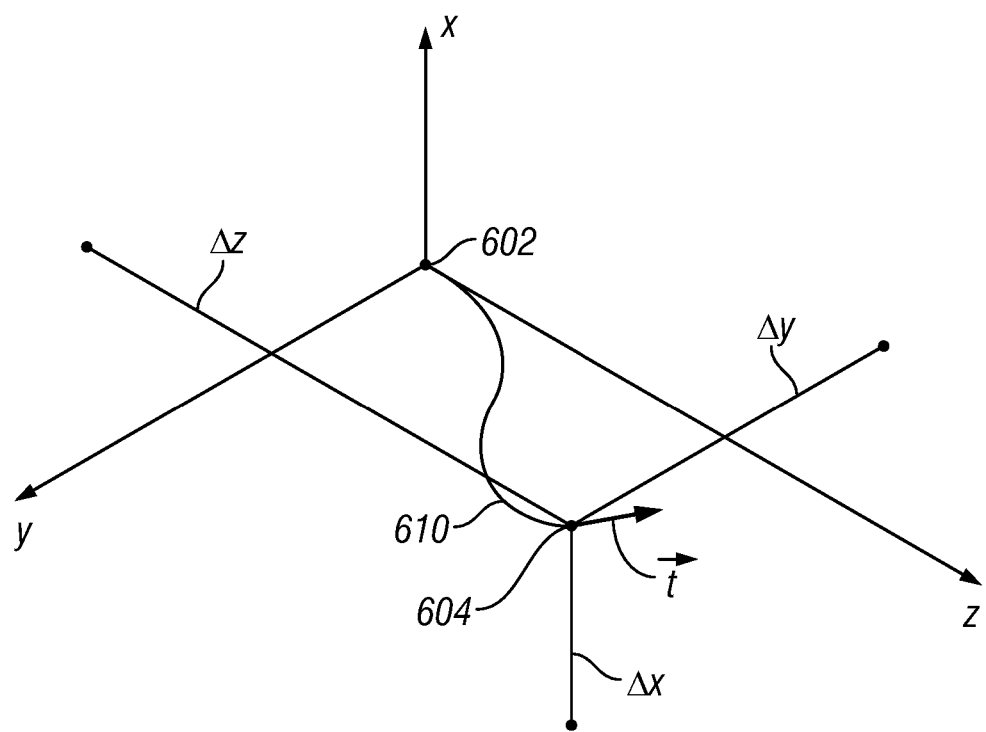

In accordance with aspects of the invention, the position and orientation of each shape sensing segment end is determined with respect to the reference frame defined at the corresponding segment start. FIGS. 6A and 6B are diagrammatic views that illustrate determining segment end position and orientation. In FIG. 6A, an illustrative shape sensing segment 600 of a fiber is shown. Segment 600 begins at segment start $L_1$ and ends at segment end $L_1+s_1$. A Cartesian segment start reference frame is defined at segment start $L_1$ as described above. The position of the segment end is identified by the distance change along each of the reference frame's axes; i.e., the position of the segment end with respect to the segment start reference frame is $\Delta x$, $\Delta y$, $\Delta z$ as shown in FIG. 6A. The orientation of the segment end is identified by tangent unit vector $\vec{t}$ as depicted, whose three scalar components are the three direction cosines $t_x$, $t_y$, $t_z$ with respect to the Cartesian reference frame. In FIG. 6A, segment 600 is shown with a simple, planar bend. But position and orientation may be determined for fiber segments having multiple bends within the three dimensions of the reference frame.

FIG. 6B shows another illustrative shape sensing segment 610 that has multiple bends in multiple planes within the segment start reference frame. Segment 610 begins at segment start $L_1$ and ends at segment end $L_1+s_1$. A segment start reference frame is defined at segment start $L_1$ as described above. And, as described with reference to FIG. 6A, the position and orientation of segment end $L_1+s_1$ are identified as $\Delta x$, $\Delta y$, $\Delta z$, and $\vec{t}$, as shown in the drawing.

Thus, in accordance with aspects of the invention, strain information for each shape sensing segment is used to determine the position and orientation of the segment end independently of the path the fiber takes between the segment start and the segment end. This fiber path independence is used to an advantage for sensing the relative positions and orientations of links in a kinematic chain, e.g., a robot arm with one or more actively controlled (e.g., servomotor actuated) joints.

A. Computation Example for Three Cores

The following is an illustration of computations carried out by an electronic data processing unit. Skilled individuals will understand that many hardware, firmware, and software options exist for constructing an electronic data processing unit, and that implementation of necessary computations will be routine in light of this description.

The expression for the local strain $\epsilon(s)$ is written as a function of distance along a given fiber core, $$\epsilon_n = \epsilon(\Delta d n) \tag{1}$$

where $\Delta d$ is the distance increment per index n. The $\Delta d$ value is set by the resolution of the OFDR-based interrogator. For instance the local strain $\epsilon(s)$ as a function of distance along each fiber core is obtained by making use of an "Optical Backscatter Reflectometer", a commercially available product from Luna Innovations Incorporated, Roanoke, Va., for each core. Such a device is able to output the phase derivative of the reflected light as a function of the distance along the fiber core, as shown in *Optical Backscatter Reflectometer User Guide* Chaps 5-6, 33-60 (Luna Technologies, Inc. 2004) (Document version 1.0 for OBR control software version 0.42 Beta), which is incorporated herein by reference. Such Phase Derivative information is proportional to the desired local strain $\epsilon(s)$ in (1).

For bend calculations, the differential strains between the cores are needed. For three cores, the required differential strains are:

$$\Delta \epsilon_{p,n} = \epsilon_{2,n} - \epsilon_{1,n} \tag{2a}$$

$$\Delta \epsilon_{q,n} = \Delta_{3,n} - \epsilon_{1,n} \tag{2b}$$

where $\Delta \epsilon_p$ and $\Delta \epsilon_q$ designate the two differential strain arrays. These differential strains can then be converted into local bends in an ortho-normal coordinate system by using a simple linear transformation, $$\begin{bmatrix} \theta_{x,n} \\ \theta_{y,n} \end{bmatrix} = \begin{bmatrix} m_{px} & m_{qx} \\ m_{py} & m_{qy} \end{bmatrix} \begin{bmatrix} \Delta \epsilon_{p,n} \\ \Delta \epsilon_{q,n} \end{bmatrix} \tag{3a}$$

The m-matrix $\overline{m}$ is a full description of the multi-core fiber, capturing the effects of the locations of the cores and the initial rotational orientation of the fiber in the coordinate system.

Next, these two rotation values are used to create a rotation matrix equal to the product of a first rotation of an angle $\theta_{x,n}$ around the x-axis and a second rotation of $\theta_{y,n}$ around the y-axis according to the equations:

$$\overline{\overline{R}}_{x,n} = \begin{bmatrix} 1 & 0 & 0 \\ 0 & \cos\theta & -\sin\theta \\ 0 & \sin\theta & \cos\theta \end{bmatrix} \tag{4a}$$

-continued $$\overline{\overline{R}}_{y,n} = \begin{bmatrix} \cos\theta & 0 & \sin\theta \\ 0 & 1 & 0 \\ -\sin\theta & 0 & \cos\theta \end{bmatrix}$$

$$\overline{\overline{R}}_n = \overline{\overline{R}}_{x,n}\overline{\overline{R}}_{y,n}$$

For small angle approximation, the above expression simplifies to:

$$\overline{\overline{R}}_n = \begin{bmatrix} 1 & 0 & \theta_{x,n} \\ 0 & 1 & \theta_{y,n} \\ -\theta_{x,n} & -\theta_{y,n} & 1 \end{bmatrix} \quad (5a)$$

where, because a first order small angle approximation is used, $\overline{\overline{R}}_n$ is a valid rotation matrix only if $\theta_x \ll 1$ and $\theta_y \ll 1$.

If sufficiently small spatial increments are used, the above conditions are not difficult to satisfy. This rotation matrix is then moved into the coordinate system at the $n^{th}$ position on the fiber. In this way, the calculations are iterated to walk down the length of the fiber, reconstructing the tangent vector, as well as the vectors defining the rotational coordinate system, along the way. The iterative equation is, $$\overline{\overline{C_{n+1}}} = \overline{\overline{C_n R_n}} \quad (6)$$

Or, for the linearized case, $$\begin{bmatrix} c_{11} & c_{12} & c_{13} \\ c_{21} & c_{22} & c_{23} \\ c_{31} & c_{32} & c_{33} \end{bmatrix}_{n+1} = \begin{bmatrix} c_{11} & c_{12} & c_{13} \\ c_{21} & c_{22} & c_{23} \\ c_{31} & c_{32} & c_{33} \end{bmatrix}_{n} \begin{bmatrix} 1 & 0 & \theta_y \\ 0 & 1 & -\theta_x \\ -\theta_y & \theta_x & 1 \end{bmatrix}_n \quad (7a)$$

And so, the coordinate system at any location along the array is given by, $$\overline{\overline{C}}_p = \overline{\overline{C}}_0 \overline{\overline{R}}_0 \overline{\overline{R}}_1 \overline{\overline{R}}_2 \ldots \overline{\overline{R}}_p = \overline{\overline{C}}_0 \prod_{n=0}^{p} \overline{\overline{R}}_n \quad (8)$$

The initial value of this coordinate system matrix, $$\overline{\overline{C}}_0 = \begin{bmatrix} c_{11} & c_{12} & c_{13} \\ c_{21} & c_{22} & c_{23} \\ c_{31} & c_{32} & c_{33} \end{bmatrix}_0 \quad (9)$$

describes the initial orientation of the fiber in the exterior coordinate system. If the fiber is initially aligned along the z-axis, the matrix will be, $$\overline{\overline{C}}_0 = \begin{bmatrix} \sin\beta & -\cos\beta & 0 \\ \cos\beta & \sin\beta & 0 \\ 0 & 0 & 1 \end{bmatrix}_0 \quad (10)$$

In the description above, the first two vectors still have one degree of freedom, which is the rotation of the fiber around its axis—the same rotational degree of freedom in the m-matrix above. This is because with three cores we cannot sense the fiber rotation around its axis. In many implementations, this situation is not generally a problem, because it will generally be taken care of automatically by the way the fiber is embedded in or associated with the kinematic chain and by calibration. Further, it means that complete generality can be retained even if the initial matrix is restricted to be, $$\overline{\overline{C}}_0 = \begin{bmatrix} 1 & 0 & 0 \\ 0 & 1 & 0 \\ 0 & 0 & 1 \end{bmatrix}_0 \quad (11)$$

B. Computation Example for Four Cores

For the case of four cores, as illustrated in FIG. 4B for instance, a similar derivation is possible, and it can be shown that in such a case also the fiber rotation around its axis can be measured. With four cores, $$\Delta\epsilon_{p,n} = \epsilon_{2,n} - \epsilon_{1,n} \quad (2a)$$

$$\Delta\epsilon_{q,n} = \epsilon_{3,n} - \epsilon_{1,n} \quad (2b)$$

$$\Delta\epsilon_{r,n} = \epsilon_{4,n} - \epsilon_{1,n} \quad (2c)$$

where $\Delta\epsilon_{p,n}$, $\Delta\epsilon_{q,n}$, and $\Delta\epsilon_{r,n}$ designate the three differential strain arrays. These differential strains are then converted into local bends in an ortho-normal coordinate system using a simple linear transformation, $$\begin{bmatrix} \theta_{x,n} \\ \theta_{y,n} \\ \theta_{z,n} \end{bmatrix} = \begin{bmatrix} m_{px} & m_{qx} & m_{rx} \\ m_{py} & m_{qy} & m_{ry} \\ m_{pz} & m_{qz} & m_{rz} \end{bmatrix} \begin{bmatrix} \Delta\varepsilon_{p,n} \\ \Delta\varepsilon_{q,n} \\ \Delta\varepsilon_{r,n} \end{bmatrix} \quad (3b)$$

The m-matrix $\overline{\overline{m}}$ is a full description of the multi-core fiber, capturing the effects of the locations of the cores and the initial rotational orientation of the fiber in the coordinate system.

These three rotation values are used to create a rotation matrix equal to the product of a first rotation of an angle $\theta_{x,n}$ around the x-axis, a second rotation of $\theta_{y,m}$ around the y-axis, and a third rotation of $\theta_{z,n}$ around the z-axis according to the equations:

$$\overline{\overline{R}}_{x,n} = \begin{bmatrix} 1 & 0 & 0 \\ 0 & \cos\theta & -\sin\theta \\ 0 & \sin\theta & \cos\theta \end{bmatrix} \quad (4b)$$

$$\overline{\overline{R}}_{y,n} = \begin{bmatrix} \cos\theta & 0 & \sin\theta \\ 0 & 1 & 0 \\ -\sin\theta & 0 & \cos\theta \end{bmatrix}$$

$$\overline{\overline{R}}_{z,n} = \begin{bmatrix} \cos\theta & -\sin\theta & 0 \\ \sin\theta & \cos\theta & 0 \\ 0 & 0 & 1 \end{bmatrix}$$

$$\overline{\overline{R}}_n = \overline{\overline{R}}_{x,n}\overline{\overline{R}}_{y,n}\overline{\overline{R}}_{z,n}$$

For small angle approximation, the above expression simplifies to:

$$\overline{\overline{R}}_n = \begin{bmatrix} 1 & -\theta_{z,n} & \theta_{x,n} \\ \theta_{z,n} & 1 & \theta_{y,n} \\ -\theta_{x,n} & -\theta_{y,n} & 1 \end{bmatrix} \quad (5b)$$

where, because a first order small angle approximation is used, $\overline{\overline{R}}_n$ is a valid rotation matrix only if $\theta_x \ll 1$ and $\theta_y \ll 1$ and $\theta_z \ll 1$.

If sufficiently small spatial increments are used, the above conditions are not difficult to satisfy. This rotation matrix is then moved into the coordinate system at the $n^{th}$ position on the fiber. In this way, the calculations are iterated to walk down the length of the fiber, reconstructing the tangent vector, as well as the vectors defining the rotational coordinate system, along the way. The iterative equation is the same as for the three core case, $$\overline{\overline{C_{n+1}}} = \overline{\overline{C_n R_n}}$$

Or, for the linearized case, $$\begin{bmatrix} c_{11} & c_{12} & c_{13} \\ c_{21} & c_{22} & c_{23} \\ c_{31} & c_{32} & c_{33} \end{bmatrix}_{n+1} = \begin{bmatrix} c_{11} & c_{12} & c_{13} \\ c_{21} & c_{22} & c_{23} \\ c_{31} & c_{32} & c_{33} \end{bmatrix}_n \begin{bmatrix} 1 & -\theta_z & \theta_y \\ \theta_z & 1 & -\theta_x \\ -\theta_y & \theta_x & 1 \end{bmatrix}_n \quad (7b)$$

And so, the coordinate system at any location along the array is given by, $$\overline{\overline{C}}_p = \overline{\overline{C}}_0 \overline{\overline{R}}_0 \overline{\overline{R}}_1 \overline{\overline{R}}_2 \ldots \overline{\overline{R}}_p = \overline{\overline{C}}_0 \prod_{n=0}^{p} \overline{\overline{R}}_n \quad (8)$$

The initial value of this coordinate system matrix, $$\overline{\overline{C}}_0 = \begin{bmatrix} c_{11} & c_{12} & c_{13} \\ c_{21} & c_{22} & c_{23} \\ c_{31} & c_{32} & c_{33} \end{bmatrix}_0 \quad (9)$$

describes the initial orientation of the fiber in the exterior coordinate system. If the fiber is initially aligned along the z-axis, complete generality can be retained even if the initial matrix is restricted to be, $$\overline{\overline{C}}_0 = \begin{bmatrix} 1 & 0 & 0 \\ 0 & 1 & 0 \\ 0 & 0 & 1 \end{bmatrix}_0 \quad (11)$$

C. Computation Example for Three and Four Cores

The mathematical treatment that proceeds from now on is identical for both the three and four core fiber cases in the above examples.

The tangent vector $\vec{t}$ is the last column of the $\overline{\overline{C}}$ matrix, $$\vec{t} = \overline{\overline{C}} \cdot \begin{bmatrix} 0 \\ 0 \\ 1 \end{bmatrix} \quad (12)$$

Accordingly, the tangent vector at any particular point is the product of all of the previous rotation vectors, $$\vec{t}_p = \overline{\overline{C}}_0 \prod_{n=0}^{p} \overline{\overline{R}}_n \cdot \begin{bmatrix} 0 \\ 0 \\ 1 \end{bmatrix} \quad (13)$$

The position at any point along the fiber is the sum of all of the previous tangent vectors, multiplied by the length of fiber that they represent, $$\begin{bmatrix} x \\ y \\ z \end{bmatrix}_q = \Delta d \sum_{p=0}^{q} \vec{t}_p \quad (14)$$

Substituting in the expression for the tangent vector gives, $$\begin{bmatrix} x \\ y \\ z \end{bmatrix}_q = \Delta d \sum_{p=0}^{q} \left[ \left( \overline{\overline{C}}_0 \prod_{n=0}^{p} \overline{\overline{R}}_n \right) \cdot \begin{bmatrix} 0 \\ 0 \\ 1 \end{bmatrix} \right] \quad (15)$$

For generality, an arbitrary offset vector can be added to place the calculated coordinates into any arbitrary coordinate system.

$$\begin{bmatrix} x \\ y \\ z \end{bmatrix}_q = \Delta d \sum_{p=0}^{q} \left[ \left( \overline{\overline{C}}_0 \prod_{n=0}^{p} \overline{\overline{R}}_n \right) \cdot \hat{z} \right] + \vec{v}_0 \quad (16)$$

where, $$\vec{v}_0 = \begin{bmatrix} x_0 \\ y_0 \\ z_0 \end{bmatrix} \quad (17)$$

and, $$\hat{z} = \begin{bmatrix} 0 \\ 0 \\ 1 \end{bmatrix} \quad (18)$$

For the computation of the position and orientation of the frame of reference at the end of a segment with respect to the frame of reference at the start of the segment, $\overline{\overline{C}}_0$ is the identity matrix, and $\vec{v}_0$ is a vector of zeros, which represents the frame of reference at the start of the segment. Alternatively, the computation can be carried in another base or world frame located, for instance, at the base of the kinematic chain. In this case $\overline{\overline{C}}_0$ is the 3×3 matrix specifying the orientation of the frame of reference at the start of the segment with respect to the above-mentioned base frame, and $\vec{v}_0$ is the 3×1 vector specifying the position of the origin of the frame of reference at the start segment with respect to the above-mentioned base frame.

As mentioned above, in some instances the quantity $\Delta d$ is known from the property of the particular interferometer that is used. Alternatively, $\Delta d$ can be calibrated by laying the segment of fiber in a straight line, for instance with the use of a fixture, and comparing the computed segment tip position from equation 18 with the known segment physical length.

II. Illustrative Implementations and Embodiments

Figure 7A:
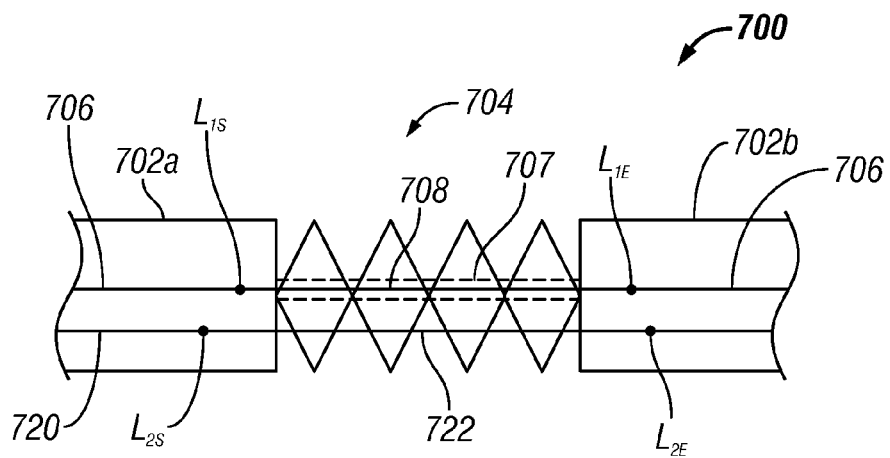
FIGS. 7A, 7B, and 7C are diagrammatic views of an illustrative kinematic chain that includes two elongate, rigid mechanical links interconnected by one or more mechanical constraints.
Figure 7B:
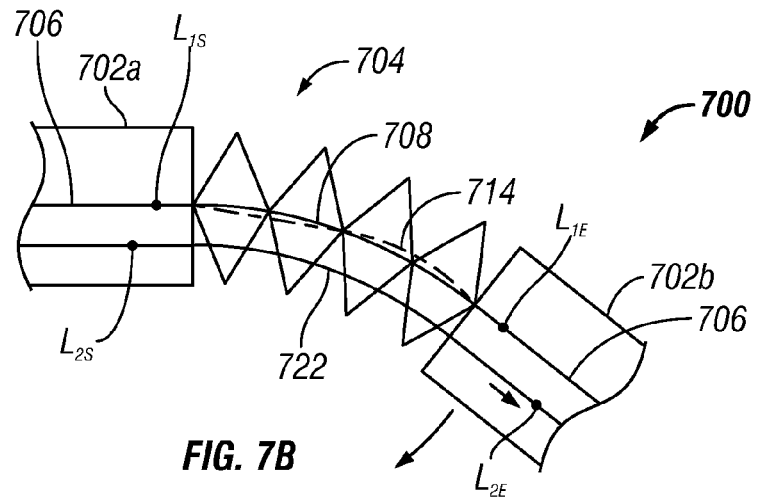
Figure 7C:
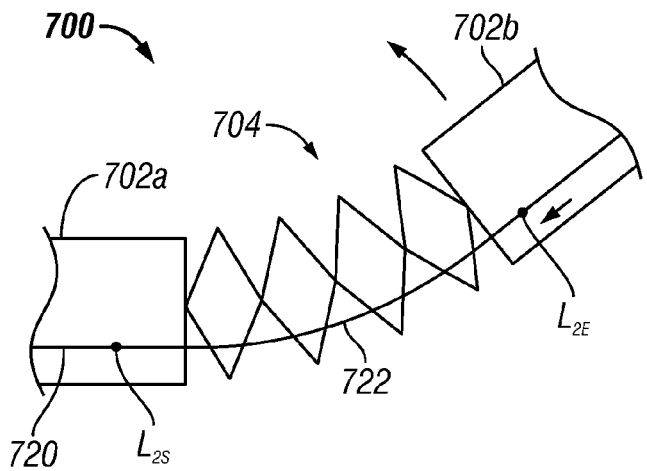

FIGS. 7A, 7B, and 7C are diagrammatic views of an illustrative kinematic chain 700 that includes two elongate, rigid mechanical links 702a, 702b interconnected by one or more mechanical constraints. The one or more mechanical constraints are illustrated as a flexible mechanical structure 704, for example. In one illustrative embodiment, flexible structure 704 is a wrist mechanism, as described in U.S. Pat. No. 6,817,974 (filed 28 Jun. 2002), which is incorporated herein by reference. Briefly, servomotor actuators control distally anchored cables that run through a flexible wrist assembly so as to move the wrist in one or two DOF's (e.g., pitch; pitch and yaw). The control cables are omitted from FIGS. 7A-7C for clarity.

As shown in FIG. 7A, a three-core, continuously FBG-configured optical fiber 706 as described above is routed through proximal mechanical link 702a, flexible structure 704, and distal mechanical link 702b. Fiber 706 is shown as being aligned with the longitudinal centerline of links 702 and flexible structure 704. In one embodiment, fiber 706 is positioned inside a flexible sheath (e.g., Teflon® FEP) (not shown) that is positioned within central lumens of 702a, 702b, and 704. Due to its centerline alignment, fiber 706 remains in position and does not slide longitudinally (surge) with reference to the links 702 when flexible structure 704 bends, as shown in FIG. 7B. Accordingly, fiber 706 may or may not be fixed in position (e.g., glued or otherwise affixed) relative to either or both links 702a,702b.

In some embodiments a resilient spring 707 is routed through the mechanical structure 704 to keep the small links in a minimum energy configuration, as described in more detail below. The spring 707 may be, for example, a helical wound coil or a resiliently bendable tube (e.g., of superelastic material), and in some instances such spring implementations may act as a conduit through mechanical structure 704 for the fiber. Skilled individuals will understand how the spring acts on the small links as mechanical structure 704 bends, although for clarity spring 707 is not shown in FIGS. 7B and 7C. Additional details of mounting and routing a shape-sensing optical fiber with reference to a link are described in concurrently filed U.S. patent application Ser. No. 12/164,297 (filed 30 Jun. 2008), which is incorporated herein by reference.

To account for small mechanical variations in kinematic chain 700 and for inaccuracies during assembly, the segment 708 that is used for shape sensing is defined to have a segment start $L_{1S}$ within proximal link 702a (i.e., proximal to the proximal end of flexible structure 704). Similarly, segment 708's segment end $L_{1E}$ is defined within distal link 702b (i.e., distal to the distal end of flexible structure 704). Defining the segment start $L_{1S}$ and segment end $L_{1E}$ within the rigid links ensures that the position and orientation of segment end $L_{1E}$ encompasses the complete bend for flexible structure 704. Further, due to real world mechanics, if fiber 706 strays from its centerline alignment as structure 704 bends, perhaps causing fiber 706 to slide inside either or both segments 702a, 702b, then the position and orientation of segment end $L_{1E}$ will still provide valid information for the pose of kinematic structure 700. For example, if segment 708 of fiber 706 follows an alternate path 714 as shown in FIG. 7B, the position and orientation information at segment end $L_{1E}$ is valid.

In some instances, however, the fiber may be offset from the kinematic chain's longitudinal centerline. As shown in FIG. 7A, for example, an illustrative fiber 720 is routed through links 702a,702b and flexible structure 704 away from the centerlines. Fiber 720's shape sensing segment 722 is defined between segment start $L_{2S}$ within proximal link 702a and segment end $L_{2E}$ within distal link 702b. For sufficient centerline offsets and bend angles, fiber 720 will slide as flexible structure 704 bends. For example, if fiber 720 is fixed in relation to proximal link 702a, then segment end $L_{2E}$ translates distally inside distal link 702b as flexible structure 704 bends, as shown in FIG. 7B. Similarly, segment end $L_{2E}$ translates proximally inside distal link 702b as flexible structure 704 bends in an opposite direction, as shown in FIG. 7C. Similar sliding of segment start $L_{2S}$ may occur if the fiber is fixed in the distal link 702b, or if the fiber is free to slide through both rigid links. As long as the segment start $L_{2S}$ and segment end $L_{2E}$ remain within their links, valid position and orientation information can be determined.

Figure 8:
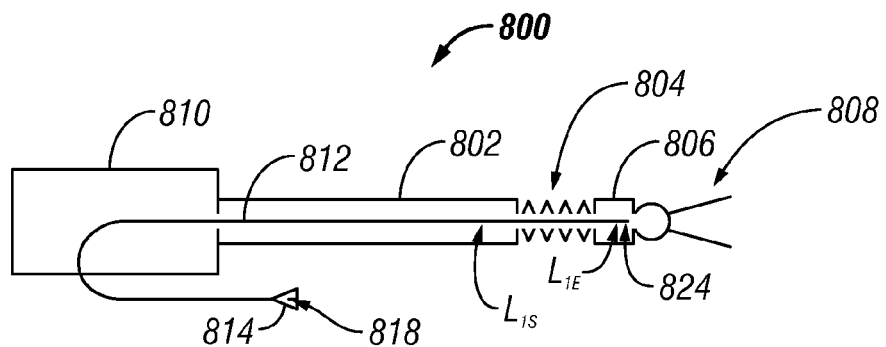
FIG. 8 is a schematic view of a minimally invasive surgical instrument.

FIG. 8 is a schematic view of a minimally invasive surgical instrument 800 that is representative of various such instruments used in the da Vinci® Surgical System, manufactured by Intuitive Surgical, Inc. of Sunnyvale, Calif., and modified in accordance with aspects of the invention. Instrument 800 includes an elongate, hollow shaft 802, a wrist mechanism 804 coupled to the distal end of shaft 802, a small distal link 806 coupled to the distal end of wrist mechanism 804, and a surgical end effector 808 (e.g., grasper, needle driver, shears, cautery tool, camera, and the like) coupled to the distal end of link 806. A force transmission mechanism 810 is coupled to the proximal end of shaft 802. Teleoperated servomotors engage transmission mechanism 810 components (e.g., rotating disks), which in turn pass activating forces through shaft 802 via cables and/or cable/hypotube assemblies to move wrist mechanism 804 and end effector 808. Additional illustrative details may be found, e.g., in U.S. Pat. No. 6,817,974 referenced above, and in U.S. Pats. No. 5,807,377 (filed 16 May 1997) and 6,461,372 (filed 8 Mar. 2000), which are incorporated herein by reference. In accordance with aspects of the invention, instrument 800 includes a three-core optical fiber 812 for shape sensing as described above.

The proximal end of fiber 812 is affixed in an illustrative connector 814, to be attached to a fiber strain interrogator unit. Connector 814 is further illustrative of embodiments in which each core of fiber 812 is coupled to an individual single core fiber, and each individual fiber is coupled to the interrogator unit. See e.g., U.S. Pat. App. Publ. No. US 2006/0013523 A1 referenced above.

Fiber 812 is then routed through, e.g., transmission mechanism 810, shaft 802, wrist mechanism 804, so that fiber 812's distal end terminates, e.g., at or near the distal end of link 806. The fiber may enter the instrument at various other positions, e.g., in the transmission mechanism or the shaft. As described above, in one aspect a base frame is defined at the proximal end 818 of fiber 812. A segment start $L_{1S}$ is defined in fiber 812 at a location proximal of wrist mechanism 804, and a segment end $L_{1E}$ is defined in fiber 812 at a location distal of wrist mechanism 804 (e.g., at distal end 824 of fiber 812. As wrist mechanism 804 bends, the position and orientation of segment end $L_{1E}$ is determined with reference to segment start $L_{1S}$. Therefore, the position and orientation of link 806 is determined with reference to shaft 802.

Figure 9:
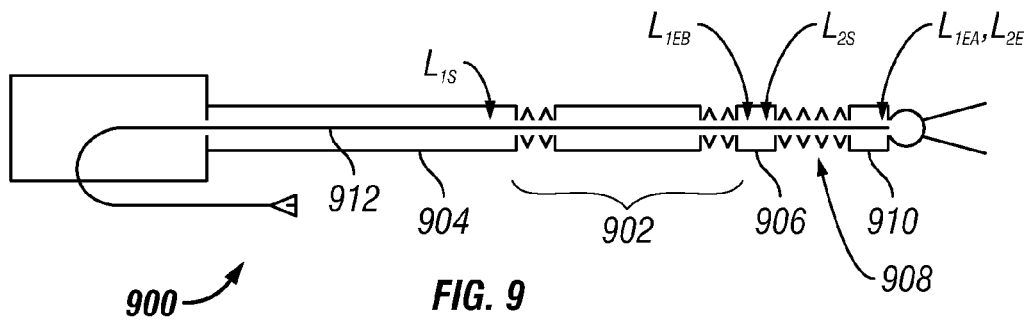
FIG. 9 is a schematic view of another minimally invasive surgical instrument.
Figure 9A:
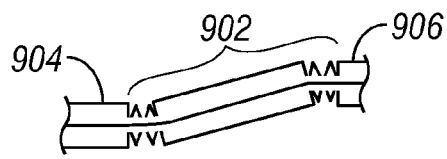
FIG. 9A is an illustrative schematic of parallel motion mechanism in a displaced pose.
Figure 9B:
FIGS. 9B and 9C are elevation views of an illustrative embodiment showing the parallel motion mechanism in line with a shaft of the surgical instrument (FIG. 9B) and displaced in position (FIG. 9C).
Figure 9C:
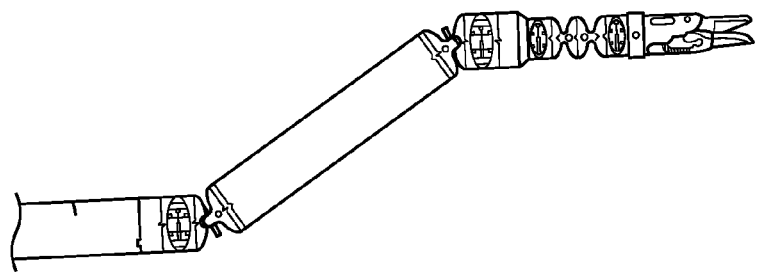

FIG. 9 is a schematic view of another illustrative minimally invasive surgical instrument 900. Surgical instrument 900 includes several components (e.g., shaft, cables, wrist mechanism, end effector) similar to those of surgical instrument 800. Surgical instrument 900 also includes a parallel motion mechanism 902 between shaft 904 and link 906, in addition to a flexible wrist mechanism 908 between link 906 and distal end link 910. Parallel motion mechanism 902 functions to change link 906's position (e.g., heave, sway) without changing link 906's orientation with respect to shaft 904. FIG. 9A is an illustrative schematic of parallel motion mechanism 902 in a displaced pose, and FIGS. 9B and 9C are elevation views of an illustrative embodiment showing the parallel motion mechanism in line with shaft 904 (FIG. 9B) and displaced in position (FIG. 9C). Details of parallel motion mechanism 902 are described in U.S. Pat. Appl. Pub. No. US 2008/0065102 A1 (filed 13 Jun. 2007), which is incorporated herein by reference.

Referring to FIG. 9, multi-core fiber 912 is routed through the instrument 900 components in a manner similar to that described for instrument 800. In one aspect, a single shape sensing segment is defined between segment start $L_{1S}$ and segment end $L_{1E4}$. This single shape sensing segment includes parallel mechanism 902, link 906, wrist mechanism 908, and at least a portion of distal link 910. Alternatively, a first shape sensing segment is defined between segment start $L_{1S}$ and segment end $L_{1EB}$, and a second shape sensing segment is defined between segment start $L_{2S}$ and segment end $L_{2E}$. The first shape sensing segment is used to determine changes in position and orientation that result from moving parallel motion mechanism 902. The second shape sensing segment is used to determine changes in position and orientation that result from moving wrist mechanism 908. As shown in FIG. 9, in one aspect segment end $L_{1EB}$ and segment start $L_{2S}$ are not coincident. In this aspect the spatial relationship between segment end $L_{1EB}$ and segment start $L_{2S}$ is known because they are both in an unchanging relationship within rigid link 906. In some aspects, however, a segment end and a segment start may be coincident or may overlap, as described above.

For a kinematic chain with long, rigid links, data processing resources, and more importantly the total length of FBG's in the fiber, may be conserved by defining shape sensing segments to cover only the chain's bendable parts, as illustrated in FIGS. 3B and 3C, or as in FIGS. 3D and 3E. There is no need to process strain information to determine the unchanging shape of such links, and a priori mechanical information in conjunction with the information from the shape sensing segments can be used to determine the chain's pose.

Since the position and orientation of the distal end of instrument 900 is determined by sensing the shape of a fiber segment, since the mechanical characteristics (e.g., link dimensions, positions and orientations of rotational axes in revolute joints, and the like) of the kinematic chain in the instrument are known, and since the kinematic chain does not contain redundant degrees of freedom, inverse kinematic calculations are used to determine the instrument's pose.

Figure 10:
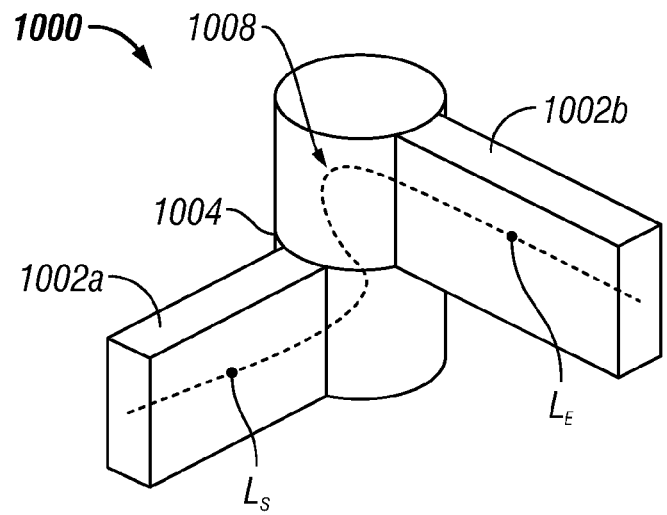
FIG. 10 is a diagrammatic view of a kinematic chain that includes two links interconnected by a revolute joint.

FIG. 10 is a diagrammatic view of a kinematic chain 1000 that includes two links 1002a,1002b interconnected by a revolute joint 1004. A shape sensing optical fiber 1006 in accordance with aspects of the invention is shown in phantom line passing through link 1002a, joint 1004, and link 1002b. As shown in FIG. 10, a portion 1008 of fiber 1006 moves freely within joint 1004. Shape sensing as described herein is used to determine position and orientation of segment end $L_E$ defined within link 1002b with reference to segment start $L_S$ defined within link 1002a. This embodiment is illustrative of shape sensing as described herein applied to various kinematic chain configurations. It can be seen that a similar configuration can be used for a prismatic joint between two links, as long as a sufficient loop of fiber is available to accommodate the prismatic joint's movement. And, aspects of the invention are not limited to kinematic chains that have long, rigid links coupled by single-axis revolute joints.

Another class of medical devices, such as endoscopes or catheter guide devices, are based on flexible structures, as described above. Snake-like structures with short, discrete components can be effectively approximated as a continuously bending element of constant or variable length as determined by the loads on the structure's longitudinal (end-to-end) axis.

In such snake-like mechanisms, the multi-core fiber can be run along or inside the device's centerline in a way similar to that described above with reference to FIG. 7A, and consequently the fiber does not need to slide as the structure bends. Alternatively, the fiber can run (e.g., in a conduit) at an offset from and parallel to the centerline in a manner similar to that described above with reference to FIGS. 7B and 7C, or it may run along a helicoidal path around the centerline.

For snake-like mechanisms, the number of controlled DOF's is usually much smaller than the number of actual mechanical links, and thus the mechanism's actual DOF's are redundant. In some cases the redundancy problem is solved by using a central spring element that forces the links to assume the minimum energy configuration compatible with the controlled DOF's (at least absent external forces along the snake body and statically). For example, a pair of controlled DOF's under this configuration can set the final orientation change over a set of contiguous links in the pitch and yaw directions. Therefore, for flexible devices (both snake-like and continuously bending), a shape sensing segment is defined for each length of the device that is controlled by one or more DOF's. For example, if a 10 cm length of the device is controllable in pitch, and an immediately adjacent 10 cm length of the device is controllable in yaw (or pitch, or some other orientation or position), then each controllable length of the device will have a corresponding shape sensing segment defined. If a 10 cm length is controllable in both pitch and yaw, then the length will still have a single corresponding shape sensing defined. If controllable lengths of a device overlap (e.g., a length controllable in yaw begins at a midpoint of a length controllable in pitch), then each overlapping controllable length will have a corresponding shape sensing segment defined.

Figure 11:
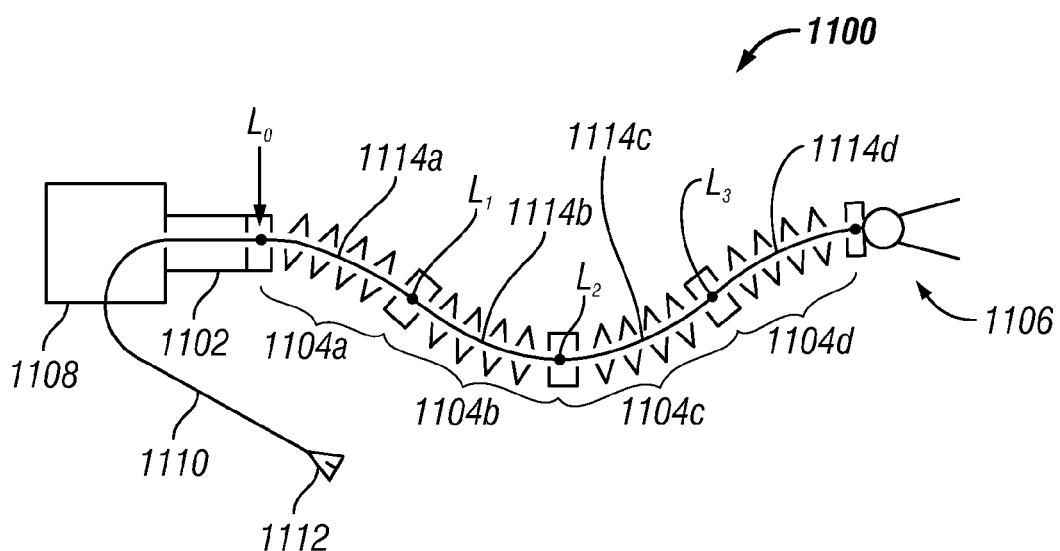
FIG. 11 is a schematic view of a kinematic chain that is illustrative of kinematic chains made of two or more flexible mechanical sections.

FIG. 11 is a schematic view of a kinematic chain 1100 that is illustrative of kinematic chains made of one, two, or more flexible mechanical sections. As shown in FIG. 11, kinematic chain 1100 has a base section 1102, four flexible sections 1104a-1104d coupled in line distally of base section 1102, and an illustrative distal end effector 1106 (e.g., grasper, needle driver, shears, cautery tool, camera, and the like) coupled to the distal end of the most distal section 1104d. In some cases, the end effector may be omitted, and kinematic chain 1100 may function as a guide that allows other mechanical devices to be routed through, over, or adjacent chain 1100. An actuator mechanism 1108 is coupled to the proximal end of base section 1102. Actuator mechanism 1108 includes components (e.g., servomotors, hand-operated wheels) coupled to cables (not shown) that are coupled to the various flexible sections 1104. Tension on the cables causes associated flexible sections 1104 to bend in one or more directions. U.S. Pats. No. 4,873,965 (filed 15 Jul. 1988) and 5,174,276 (filed 28 Jun. 1991), which are incorporated herein by reference, are illustrative of such mechanisms.

In a manner similar to that described above, a three-core shape sensing optical fiber 1110 is routed through the base section 1102 and the flexible sections 1104a-1104d. A proximal end connector 1112 is used to connect fiber 1110 to an interrogator unit, as described above. In accordance with aspects of the invention, at least four shape sensing segments are defined in fiber 1110. Each of the shape sensing segments is associated with one of the flexible sections 1104. Shape sensing segment 1114a is associated with flexible section 1104a and starts at segment start $L_0$, thereby demonstrating that a shape sensing segment may begin at the origin of the base reference frame. Likewise, segment 1114b is associated with flexible section 1104b and starts at segment start $L_1$, segment 1114c is associated with flexible section 1104c and starts at segment start $L_2$, and segment 1114d is associated with flexible section 1104d and starts at segment start $L_3$. As described above, several of the segment starts and ends may be defined at the same location in fiber 1110, or short, additional segments may be defined between the various segment ends and starts.

As described above, the position and orientation of each segment end is determined with reference to a reference frame at its corresponding segment start. This position and orientation information is aggregated to determine the position and orientation of the distal end of section 1104*d* (and therefore, in this example, end effector 1106) with reference to a base reference frame associated with base 1102. Further, since the position and orientation of the distal end of the flexible device in FIG. 11 is determined by sensing the shape of a fiber segment, since the mechanical characteristics (e.g., link dimensions, positions and orientations of rotational axes in revolute joints, and the like) of the kinematic chain in the snake device are known, and since the kinematic chain redundant DOF's can be computed to minimize the center spine elastic potential energy, inverse kinematic calculations are used to determine the flexible device's pose. Determining the pose is important, for example, in surgical applications in which it is necessary to avoid collision with another instrument or with certain tissue structures.

In all the cases described above and depicted in FIGS. 7-11, presented in accordance with aspects of the invention, the position of the kinematic chain is estimated by combining three sources of information: (i) the Cartesian information produced by the shape sensor for each of the defined segments; (ii) the a priori knowledge of the kinematic model of the kinematic chain (e.g., as stored in a readable electronic memory); and (iii) the a priori knowledge of the nature of the mechanical constraints between the kinematic chain and the shape sensing fiber at the start and end of the segment (e.g., as stored in a readable electronic memory). A general description of the methodology is presented and several relevant applications are described below.

The Cartesian information produced by the shape sensor consists of the position and orientation of the end point of each of the defined segments with respect to each segment's initial frame of reference. The position is a 3D vector $\vec{p}_s$ and the orientation is represented for instance by the tangent vector $\vec{t}_s$. An additional roll angle $r_s$ can be used to specify the rotation of the fiber around its axis at the end of the segment. All three quantities are computed for each segment as described in equations 13 and 15 above.

The a priori knowledge of the kinematic model of the kinematic chain is represented by a forward kinematic model that allows computing the Cartesian position and orientation of the frame of reference at the end of the segment as a function of a vector $\vec{q}$ of n joint variables $[\vec{q}_1 \ldots \vec{q}_n]$ according to:

$$[p_s t_s] = f\text{kin}(\vec{q}) \quad (19)$$

The kinematic model of a kinematic chain is easily constructed according to known methods. For instance, the procedure described in John J. Craig, *Introduction to Robotics: Mechanics and Control* (Pearson Education Ltd. 2004), which is incorporated herein by reference, may be used. Denavit Hartenberg frames of reference are assigned to each joint of the chain, the base frame of reference is defined as the segment start frame of reference, and the tool tip frame of reference is defined as the segment end frame of reference. Both rotational and translational (prismatic) joints can be easily handled by this well-known method. The number of joints spanned by the defined segment is arbitrary. As examples, the following cases are described below: (i) a single DOF, as in the joint illustrated by FIG. 10; (ii) two DOF's, as in the wrist mechanisms illustrated in FIGS. 7A, 7B, 7C, and 8; (iii) two DOF's, as in the mechanism illustrated in FIG. 9A; (iv) four DOF's, as in the mechanisms illustrated in FIGS. 9-9C; (v) six DOF's; and (vi) large (>6) numbers of DOF's as in the mechanism illustrated in FIG. 11. In this last case, the kinematic model is completed by a scalar function that represents the potential energy of the spring backbone as a function of the joint variables $\vec{q}$: $E(\vec{q})$.

The a priori knowledge of the nature of the mechanical constraints between the kinematic chain and the fiber at the start and the end of the segment enables the following fiber attachment cases to be distinguished. In the first case, the fiber is mechanically attached at both ends of the segment. In this first case, the fiber shape sensor is measuring a position and orientation of the end of the fiber segment that is directly related to the position and orientation of the link of the kinematic chain embedding the end of the fiber segment. Hence, information about the six DOF's of the links is obtained if a twist sensing fiber is used, while information about five DOF's of the link is obtained if a 3 core fiber is used. In the second case, the fiber is attached at the start of the segment and free to slide at the end of the segment, for example in a cylindrical conduit embedded in a link of the kinematic chain. In this second case the fiber shape sensor is measuring the position and orientation in space of the conduit in the link of the kinematic chain embedding the end of the fiber segment. If the conduit is cylindrical and tightly fits around the fiber, then information about four DOF's of the links is obtained. The third case is similar to the second case, except the fiber is attached at the end of the segment and is free to slide at the start of the segment. As in the second case, information about four DOF's of the links is obtained.

In the three illustrative fiber attachment cases above, the fiber is not required to go through the centerline of the kinematic chain or along a path specified in any way. If assumptions can be made about the path followed by the fiber, such as that the path does not change in length or that the path lies in a plane or in a set of planes, then more specialized approaches described below can be also used. For example, if the start or end of the fiber is guided within the links of the kinematic chain in slits that tightly constrain the fiber in only a plane of the embedding links, then information about three DOF's of the links is obtained.

The three sources of information described above are combined together in a goal function that is then numerically minimized to compute the best estimate for the joint variables $\vec{q}$.

The minimization of the nonlinear goal function can be achieved with known techniques, such as gradient descent methods, Newton Rapson methods, and other methods as described, for instance, in Deepak Tolani, Ambarish Goswami, & Norman I. Badler, *Real-Time Inverse Kinematics Techniques for Anthropomorphic Limbs*, 62 Graphical Models 353-388 (September 2000) and in N. I. Badler, K. Manoochehri, & G. Walters, *Articulated Figure Positioning by Multiple Constraints*, 7 IEEE Computer Graphics and Applications 28-38 (June 1987), which are incorporated herein by reference. The minimization results are different depending on the relationship between the number of DOF's of the kinematic chain and the number of DOF's of information that the shape sensor is able to gather about the link.

In particular, three sensed/actual DOF cases can be distinguished. In the first sensed/actual DOF case, the number of kinematic DOF's is lower than the number of sensed DOF's. In this first case the position $\vec{q}$ of the kinematic chain can be determined and also the noise in the $\vec{q}$ from the sensor can be minimized by merging together the redundant sensor information, which can also be weighed differently according to its noise to signal ratio. In the second sensed/actual DOF case, the number of kinematic DOF's is equal to the number of sensed DOF's. In this second case the minimization is converging to a unique solution for the vector $\vec{q}$, and the minimization algorithm is a kind of inverse kinematics algorithm that is well described in the robotics literature (see e.g., *Springer Handbook of Robotics* (Bruno Siciliano & Oussama Khatib eds., Springer 2008), which is incorporated herein by reference). In the third sensed/actual DOF case, the number of kinematic DOF's is higher than the number of sensed DOF's. In such a case, the vector $\vec{q}$ cannot be uniquely determined (strictly speaking). In this third case, therefore, the kinematic chain should be split into two or more parts, and for each part a shape sensing segment of fiber should be defined to produce position and orientation information so that no ambiguity is possible about the joint positions.

Further, in this third sensed/actual DOF case, two special subcases can be solved by using just one sensing segment of fiber. The first subcase concerns a kinematic chain representing flexible kinematics of a device with a central spring. In this first subcase, the potential energy $E(\vec{q})$ of the spring can be minimized as part of the overall minimization, and thus the whole vector $\vec{q}$ can be uniquely determined under the restrictive hypothesis of no external forces acting on the mechanical structure. The second subcase concerns a kinematic chain whose links have constraints to their motions that are in addition to the ones from the joints. For example, there may be constraints due to mechanical construction, such as from cables running through the links with coupled motions, as in a snake-like wrist composed of four links and four joints but having only two degrees of freedom as a result of the kinematic coupling enforced by the actuation cables. In this second subcase, the additional constraints reduce the kinematic DOF's, and the case is reduced to the first or second sensed/actual DOE cases described above.

The following specific examples illustrate the outlined methods for selected cases. It should be understood that these examples are not limiting, and that aspects of the invention may be applied in other than the selected cases below.

A. EXAMPLE 1

Referring to FIG. 7, a kinematic chain of four links coupled to retain two DOF's of bending can be described by an overall kinematic model:

$$[p_k t_k] fkin(\vec{q}_1, \vec{q}_2) \tag{20}$$

The sensing segment start frame is defined in the first link, and the sensing segment end frame is defined in the second link. The three cases of the sensing fiber attached to both links, attached in the first link and unconstrained at the tip to slide in a tight cylindrical conduit in the second link, or attached in the second link and unconstrained to slide in a tight cylindrical conduit in the first link, can all be described by the goal function:

$$\text{Min with respect to } \vec{q}_1, \vec{q}_2 \text{ of } \{Abs(t_s - t_k)\} \tag{21}$$

This function describes that the fiber segment end is constrained to have the same orientation with respect to the fiber segment start as the second link has with respect to the first link. Given that the orientation measurement $t_s$ has two DOF's (it is a unit vector), $\vec{q}_1$ and $\vec{q}_2$ are uniquely determined.

B. EXAMPLE 2

Referring to FIG. 10, a single-DOE rotational joint $\vec{q}_1$ can be described by the kinematic model of the form:

$$[p_k t_k] = fkin(\vec{q}_1) \tag{22}$$

The sensing segment start frame is defined in the first (proximal) link, and the sensing segment end frame is defined in the second (distal) link. The sensing fiber may be attached in the first link and unconstrained to slide in a tight, cylindrical conduit in the second link, or the sensing fiber may be attached in the second link and unconstrained to slide in a tight, cylindrical conduit in the first link. The associated goal function is:

$$\text{Min with respect to } \vec{q}_1 \text{ of } \{Abs(t_s - t_k)\} \tag{23}$$

Given that the orientation measurement $t_s$ has two DOF's (it is a unit vector), $\vec{q}_1$ is determined, and the measurement noise can be minimized too.

In another implementation, the fiber may be constrained in a slit (rather than in a cylindrical conduit) in either or both of the proximal and distal links, with the slit(s) oriented parallel to the joint's axis of rotation. Thus, the fiber may slide sideways in the slit as well as along the link's longitudinal axis. The associated goal function is:

$$\text{Min with respect to } \vec{q}_1 \text{ of } \{Abs\lfloor(t_s-t_k)-(t_s-t_k)\cdot z_j\rfloor\} \tag{24}$$

where • indicates the scalar product. In this case, $\vec{q}_1$ is uniquely determined.

C. EXAMPLE 3

Referring to FIG. 9A, mechanism 902 illustrates a kinematic chain of seven links and additional mechanical constraints that enforce the parallelism of the output link 906 with respect to shaft 904 so that two DOF's $\vec{q}_1$ and $\vec{q}_2$ are sufficient to describe the overall kinematics according to a model of the form:

$$[p_k t_k] = fkin(\vec{q}_1, \vec{q}_2) \tag{25}$$

The sensing segment start frame is defined in the first link (shaft 904) and the sensing segment end frame is defined in the second link (link 906). The sensing fiber may be attached in the first link and unconstrained to slide in a tight, cylindrical conduit in the second link, or the sensing fiber may be attached in the second link and unconstrained to slide in a tight, cylindrical conduit in the first link. The associated goal function that describes that the fiber end segment position with respect to the fiber start segment position in the plane orthogonal to the fiber axis is equal to the position of second link with respect to the first link in the plane orthogonal to the fiber axis is:

$$\text{Min with respect to } \vec{q}_1, \vec{q}_2 \text{ of } \{Abs[(p_s-p_k)-(p_s-p_k)\cdot z_1]\} \tag{26}$$

with $z_1$ being the unit vector of the z-axis of the segment start frame. In such a case, $\vec{q}_1$ and $\vec{q}_2$ are determined uniquely from the two DOF's of measurement.

Referring now to the case illustrated in combined FIGS. 9-9C, the required position and orientation information can be sensed by defining two fiber sensing segments. The first segment senses the configuration of parallel motion mechanism 902, as described above. The second segment senses the configuration of wrist mechanism 908 (between links 906 and 910) with the methodology already described for FIG. 7.

Alternatively, especially if the two mechanisms blend into one another over a short distance, the configuration of the entire distal end of the instrument can be sensed by using a single sensing segment. The kinematic chain describing the whole distal end has two DOF's in mechanism 902 and two more in mechanism 908, as described above. Consequently, the kinematic model is specified by four kinematic parameters $\vec{q}_1, \vec{q}_2, \vec{q}_3, \vec{q}_4$ in the form:

$$[p_k t_k] = f\mathrm{kin}(\vec{q}_1, \vec{q}_2, \vec{q}_3, \vec{q}_4) \tag{27}$$

The sensing segment start frame is defined in shaft 902, and the sensing segment end frame is defined in distal link 910.

In this single-segment, four-DOF aspect, there are various ways of routing and constraining the fiber through the mechanisms, and accordingly a unique approach to the calculations is developed for each of the various ways of routing and constraining the fiber. In a first illustrative approach, the fiber is attached to both shaft 902 and link 910 and runs through a center lumen of the instrument. The goal function describing that the relative orientation and position of the fiber segment end with respect to the fiber segment start is identical to the relative orientation and position of the shaft link 902 with respect to the distal link 910 is:

$$\text{Min with respect to } \vec{q}_1, \vec{q}_2, \vec{q}_3, \vec{q}_4 \text{ of } \{w_p \cdot \mathrm{Abs}(p_s - p_k) + w_t \cdot \mathrm{Abs}(t_s - t_k)\} \tag{28}$$

with $w_p$ and $w_t$ being scalar weights that represent the relative confidence in the position data with respect to the orientation data. Accordingly, the tricore shape sensing fiber provides four DOF's of measurement that enable finding the $\vec{q}_1, \vec{q}_2, \vec{q}_3$ and $\vec{q}_4$ values and minimizing the noise.

In a second illustrative approach to routing and constraining the fiber, the fiber is allowed to slide in a tight cylindrical conduit in link 910 and is not required to run through a center lumen of the instrument. The goal function that describes that the information about the position of the fiber segment end along the fiber axis is unconstrained from the link 910 position along the same axis is:

$$\text{Min with respect to } \vec{q}_1, \vec{q}_2, \vec{q}_3, \vec{q}_4 \text{ of } \tag{29}$$

$$\left\{ w_p \cdot \mathrm{Abs}\left[\frac{(p_s - p_k)}{\mathrm{Abs}(p_s - p_k)} - t_s\right] + w_t \cdot \mathrm{Abs}(t_s - t_k) \right\}$$

In such a case, the fiber provides four DOF's of measurement which uniquely define the $\vec{q}_1, \vec{q}_2, \vec{q}_3,$ and $\vec{q}_4$ values.

In a third illustrative approach to routing and constraining the fiber, the fiber is allowed to slide in a tight cylindrical conduit in shaft link 902, is attached to link 910, and is not required to run through a center lumen of the instrument. The goal function that describes that the information about the position of the fiber segment start along the fiber axis is unconstrained from the link 902 position along the same axis is:

$$\text{Min with respect to } \vec{q}_1, \vec{q}_2, \vec{q}_3, \vec{q}_4 \text{ of } \tag{30}$$

$$\left\{ w_p \cdot \mathrm{Abs}\left[\frac{(p_s - p_k)}{\mathrm{Abs}(p_s - p_k)} - z_0\right] + w_t \cdot \mathrm{Abs}(t_s - t_k) \right\}$$

where $z_0$ is the z-axis vector of the frame of reference attached to the fiber segment start. In this approach, the fiber also provides four DOF's of measurement which uniquely define the $\vec{q}_1, \vec{q}_2, \vec{q}_3,$ and $\vec{q}_4$ values.

D. EXAMPLE 4

Referring now to FIG. 11, a kinematic chain with two or more flexible sections 1104 is shown. Each flexible section has more than six DOF's and can assume, for example, an S-shape. In each section, some of the DOF's are controlled by an actuator, for instance by means of cables driven by a teleoperated servomotor, while the movements in other DOF's are determined by the interaction of the constraints imposed by the cables and the action of a center spring element. In one implementation, the control cables set the bending of the most distal link of a flexible section 1104 (as illustrated in FIG. 11, this most distal link may be the most proximal link of the next adjacent flexible section), while the orientation of the other intermediate links in the section 1104 are set by the spring force. A kinematic model can be used to describe just the orientation of the most distal link as a function of two joint variables $\vec{q}_1$ and $\vec{q}_2$ when the spring energy is minimized. This kinematic model takes the form:

$$[p_k t_k] = f\mathrm{kin}(\vec{q}_1, \vec{q}_2) \tag{31}$$

The sensing fiber may be attached in the first (most proximal) link and unconstrained to slide in a tight, cylindrical conduit in the second (most distal) link, or the sensing fiber may be attached in the second link and unconstrained to slide in a tight, cylindrical conduit in the first link. The associated goal function that describes that the fiber segment end has the same orientation with respect to the fiber segment start that the first link has with respect to the second link is:

$$\text{Min with respect to } \vec{q}_1, \vec{q}_2 \text{ of } \{\mathrm{Abs}(t_s - t_k)\} \tag{32}$$

In this way the joint variables $\vec{q}_1$ and $\vec{q}_2$ can be uniquely determined while the orientation of the intermediate links is assumed to minimize the spring energy.

III. Illustrative System Implementations And Embodiments

Figure 12:
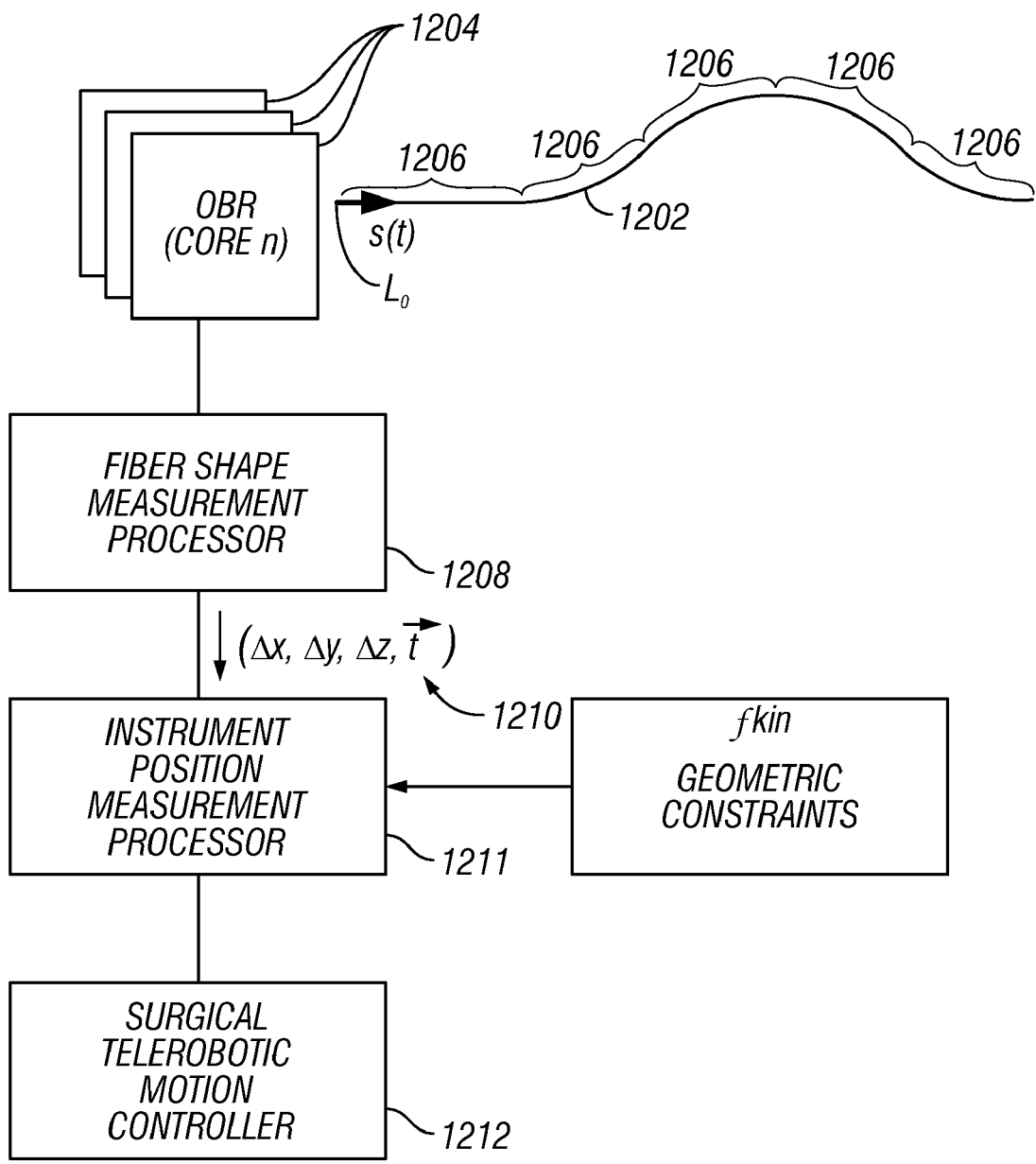
FIG. 12 is a diagrammatic view of a shape sensing system.

FIG. 12 is a diagrammatic view of a shape sensing system. In an illustrative aspect, the proximal end of a shape sensing, multi-core (e.g., 3-core) fiber 1202 as described above is coupled to an OBR interrogator 1204 using a coupling as described above to establish a base reference frame for fiber 1202. In one implementation, OBR 1204 is an "Optical Backscatter Reflectometer" and associated software purchased from Luna Innovations Incorporated, Roanoke, Va. that is included for each core of the shape sensing fiber to perform the core strain measurements based on the measurement of the phase derivative of the reflected light in each core. Each OBR 1204 provides a core strain measurement vector $\epsilon(\Delta dn)$ to a fiber shape measurement processor 1208 that provides additional electronic data processing in accordance with aspects of the invention described in equations 1 to 18 above. In an illustrative embodiment, one or more FPGA's in the OBR unit is added and/or modified in accordance with aspects of the invention. For the purposes of this description, skilled individuals will understand that the various possible electronic data processing hardware, firmware, and software combinations in the interrogator and "processors" may function as a single electronic data processing unit, which may include the a priori information as described herein in a readable electronic memory in one or more accessible locations in the interrogators/processors.

To define locations along fiber 1202, a curvilinear coordinate system s(t) is defined with an origin $L_0$ at fiber 1202's proximal end. Then, various shape sensing segment starts and ends are defined in using locations in the curvilinear reference frame to define one or more shape sensing segments 1206 (five are depicted, beginning at the proximal end and ending at the distal end of fiber 1202). As described above, the defined segments may be immediately adjacent one another (see e.g., FIG. 3A), or the defined segments may be spaced apart or overlap.

FIG. 12 also shows fiber shape measurement processor 1208 coupled to communicate (e.g., wired, wireless, optical coupling) with instrument position measurement processor 1211. As described above, fiber shape measurement processor 1208 receives strain information from each of the three OBR 1204 units and outputs bend information as $\Delta x$, $\Delta y$, $\Delta z$, and $\vec{t}$ for each of the segments 1206 in a signal 1210 to Instrument Position Measurement Processor 1211. In one illustrative aspect, the bend information for each shape sensing segment is output as seven 16-bit words. The first six of the words each contain the fixed point representation of one of the $\Delta x$, $\Delta y$, $\Delta z$, $t_x$, $t_y$, and $t_z$ values. A seventh word includes data counter, fiber identification number, shape sensing segment identification number, and fault bits. Thus the position and orientation information for each shape sensing segment is output to instrument position measurement processor 1211 in a format that is easily subject to further processing. Instrument position measurement processor 1211 also receives the instrument kinematic model fkin and the description of the geometrical constraints between the fiber and the kinematic chain of the instrument as described in Examples 1-4. Instrument position measurement processor 1211 thus performs the numerical optimization that leads to the estimate of the joint variables $\vec{q}$ for the surgical instrument as described above in Examples 1-4 and equations 19-32. The surgical telerobotic motion controller 1212 then uses the joint position measurements to control the pose of the kinematic chain whose shape is being sensed by fiber 1202 (e.g., by receiving inputs from a hand-operated controller and outputting servomotor command signals that correspond to the received inputs). The operation of motion controller 1212 is for example as described in, e.g., U.S. Pats. No. 6,493,608 (filed 7 Apr. 1999) and 6,424,885 (filed 13 Aug. 1999), and in U.S. Pat. Appl. No. US 2007/0151389 (filed 20 Dec. 2006), all of which are incorporated herein by reference, with the joint encoder input substituted with the joint position measurements from controller 1212.

Aspects of the shape-sensing invention described herein include several advantages over known shape-sensing systems. Such advantages are especially useful in aspects associated with telerobotically controlled surgical instruments, since the necessary information is provided with the precision needed for surgery.

First, the shape sensing is based on measurement of strain in the fiber along each FBG with a very high resolution—on the order of microns for fibers of 10 m—as determined by the laser source coherence length. Since the FBG's are written adjacent one another in the core, the strain measurement has a very high resolution throughout the fiber length. The resulting strain data set can be very large.

Second, the shape or state of the fiber is represented syntetically but effectively for the purpose of determining the configuration of the kinematic chain embedding the fiber (e.g., of a surgical instrument or other device embedding the fiber). The state of the fiber is represented by the state of a set of segments defined in the fiber, and the segments may be adjacent, separated, or overlapping. Each segment is defined by a start and end position along the fiber and has an associated start (base) and end frame of reference. The state of each segment of fiber is represented by the position and orientation of the end frame with respect to the segment base frame.

Third, the position and orientation of the end frame of each segment is computed from the high resolution strain measurements on each core by means of an exact tridimensional integration over the segment, with integration steps equal to the strain measurement resolution. The tridimensional integration natively produces both the position and orientation of the end frame, i.e., a six degrees of freedom measurement. The resulting full six degree of freedom Cartesian position and orientation data facilitates further computation.

Fourth, the position and orientation of the segment end frame—the segment data—is largely independent from the path taken by the length of fiber due to the high resolution of strain data and exact 3D integration.

Fifth, the segment data can be merged with a priori information about the kinematic chain (i.e., with the kinematic model of the embedding structure) to estimate the most likely position of one or more links embedding the segment of fiber.

Sixth, the nature of the mechanical constraints between the fiber and the embedding kinematic chain can be explicitly taken into account in the process of merging the a priori information about the kinematic chain with the segment data in order to provide the most likely estimate of the link positions and orientations. In this way, the sliding, twisting, or curving of the fiber in its conduit does not negatively affect measurement of the kinematic chain's shape or pose.

I claim:

1. An apparatus comprising:
a kinematic chain comprising a proximal end and a distal end flexibly coupled to the proximal end;
a shape sensing optical fiber associated with the kinematic chain, wherein a shape sensing segment in the optical fiber is defined in the fiber between the proximal end and the distal end, and wherein a three-dimensional reference frame is defined at a start location of the shape sensing segment;
an interrogator that outputs strain information associated with shape sensing segment; and
an electronic data processor that receives the strain information and outputs a Cartesian position of an end point of shape sensing segment with respect to the reference frame.

2. The apparatus of claim 1:
wherein the reference frame comprises an x-axis, a y-axis, and a z-axis; and
wherein the position is output as $\Delta x$, $\Delta y$, $\Delta z$.

* * * * *